(12) United States Patent
Ouchi

(10) Patent No.: US 6,514,215 B1
(45) Date of Patent: Feb. 4, 2003

(54) ENDOSCOPIC TISSUE COLLECTING INSTRUMENT

(75) Inventor: Teruo Ouchi, Saitama (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/678,260

(22) Filed: Oct. 3, 2000

(30) Foreign Application Priority Data

| Oct. 13, 1999 | (JP) | .......................................... 11-290445 |
| Oct. 21, 1999 | (JP) | .......................................... 11-299007 |
| Oct. 28, 1999 | (JP) | .......................................... 11-306298 |

(51) Int. Cl.⁷ .............................................. A61B 5/00
(52) U.S. Cl. ..................................................... 600/564
(58) Field of Search ......................... 600/562, 564–567, 600/104, 106, 114, 153; 606/167, 170

(56) References Cited

U.S. PATENT DOCUMENTS

| 4,010,737 A | * | 3/1977 | Vilaghy et al. ............. 600/567 |
| 5,339,828 A | * | 8/1994 | Keatin et al. ............... 600/562 |
| 5,487,392 A | | 1/1996 | Haaga |
| 5,649,547 A | * | 7/1997 | Ritchart et al. ............. 600/566 |
| 5,718,237 A | | 2/1998 | Haaga |
| 5,775,333 A | * | 7/1998 | Burbank et al. ............. 600/566 |
| 5,976,073 A | | 11/1999 | Ouchi ......................... 600/129 |
| 6,007,496 A | * | 12/1999 | Brannon ..................... 600/565 |

FOREIGN PATENT DOCUMENTS

| JP | 2551545 | 6/1997 |
| JP | 2558135 | 9/1997 |
| JP | 10216134 | 8/1998 |
| JP | 2994062 | 10/1999 |

* cited by examiner

*Primary Examiner*—Max Hindenburg
(74) *Attorney, Agent, or Firm*—Greenblum & Bernstein, P.L.C.

(57) ABSTRACT

An endoscopic tissue collecting instrument includes a needle shaft with a tip pointed forward, that has a tissue retaining recess formed in a lateral side of an area close to the tip, an outer sheath that is fitted over the needle shaft to be capable of moving back and forth and which has a blade formed at a distal end to cut off a tissue retained in the recess, and an aspiration channel communicating with the recess from a rear side, which is formed between the needle shaft and the outer sheath.

7 Claims, 18 Drawing Sheets

ENDOSCOPIC TISSUE COLLECTING INSTRUMENT

BACKGROUND OF THE INVENTION

The present invention relates to an endoscopic tissue collecting instrument suitable for use typically in a biopsy of the liver, the pancreas or other organ by being inserted into and removed from a treatment instrument insertion channel in an endoscope.

FIG. 31 shows the distal end portion of a Menghini needle used as an endoscopic tissue collecting instrument. It comprises a rod-shaped needle shaft 10 having a pointed end 11 and a tissue retaining recess 12 formed in the lateral side of an area close to the needle end 11 and into which an excised tissue specimen is retained.

A cannula or outer sheath 20 is fitted over the needle shaft 10 to be capable of moving back and forth along the longitudinal axis and it has an annular blade 21 formed on the inner circumference of the tip for cutting off the tissue retained in the recess 12.

FIGS. 32 and 33 show how a tissue specimen for biopsy is collected with the endoscopic tissue collecting instrument. First, as shown in FIG. 32, the outer sheath 20 pierced into the tissue 100 is pulled back a little so that the desired portion of the tissue 100 is caught in the recess 12. Then, as shown in FIG. 33, the outer sheath 20 is immediately pushed forward to cut off the retained portion as a tissue specimen 101.

A problem with the above-described endoscopic tissue collecting instrument is that the depth of the tissue retaining recess 12 is inevitably much smaller than the diameter of the outer sheath 20, often causing a failure to collect an adequate amount of the tissue specimen as shown in FIG. 34

That is, as shown in FIG. 34, not all of the recess 12 is filled up with the tissue specimen 101 but some part of it remains empty as shown in FIG. 34, and thus the collected tissue specimen 101 is small in amount. Further, as shown FIG. 35, when the outer sheath 20 is being pushed forward, the tissue specimen 101 is pushed aside by the outer sheath 20 to be lifted away from the recess 12. This also causes the volume of the tissue specimen 101 that can be collected in the recess 12 to be much smaller than the capacity of the recess 12.

An object, therefore, of the present invention is to provide an endoscopic tissue collecting instrument with which an adequate amount of the tissue specimen can be easily collected without increasing the size of the instrument (for example, the diameter of the outer sheath).

The Menghini tissue collecting needle as described above is made up of a simple combination of the needle shaft 10 and the outer sheath 20, and designed for use together with a rigid endoscope.

Another problem occurs if a rigid endoscope is replaced by a soft endoscope having a flexible part to be inserted into a body cavity. Since the treatment instrument insertion channel of a soft endoscope becomes tortuous as it is passed into a body cavity, a considerably high frictional resistance in the channel makes it difficult to manipulate the needle shaft 10 and the outer sheath 20 such that they are moved back and forth in small increments and independently of each other. Hence, it has been impossible to collect the desired tissue specimen in a safe and quick manner.

Another object, therefore, of the present invention is to provide an endoscopic tissue collecting instrument that is suitable for use with both a rigid and a soft endoscope and which yet can collect the desired tissue specimen in a safe and quick manner.

SUMMARY OF THE INVENTION

According to the present invention, an aspiration channel communicating with a tissue retaining recess from the rear side is formed. The aspiration channel preferably extends between the needle shaft and the outer sheath. Therefore, a large tissue specimen can be collected by aspirating it to be retained in the recess and cutting the aspirated specimen off from the other part of the tissue. In this way, an adequate amount of the tissue specimen can be easily collected without increasing the size of the instrument.

As a further advantage, since the entire length of the aspiration channel is exposed on the surface of the needle shaft, not only the formation of the aspiration channel but also the cleaning and disinfection of it after service can be accomplished with relative ease.

In a preferred embodiment, an endoscopic tissue collecting instrument comprises a needle shaft with a tip pointed forward that has a tissue retaining recess formed in the lateral side of an area close to the tip, and an outer sheath that is fitted over the needle shaft to be capable of moving back and forth and which has a blade formed at the distal end to cut off the tissue retained in the recess. An aspiration channel communicating with the recess from the rear side is formed between the needle shaft and the outer sheath.

The aspiration channel may be formed by removing or denting part of the surface of the needle shaft. This can be accomplished by cutting or denting the shaft's surface to a flat plane, making a groove in the surface or forming a hollow in the form of an inverted $\Omega$.

Preferably, a fixing mechanism is provided to ensure that the outer sheath is fixed to the needle shaft with the needle shaft projecting by a desired length from the distal end of the outer sheath. It is also preferred that an index is provided on the side closer to the operator to tell the operator that the distal end of the outer sheath is in a specified position relative to the needle shaft.

According to the present invention, an outer needle tube, an inner needle tube and an aspirating port are provided. The tissue aspirated into the outer needle tube via the tissue aspirating port formed in its lateral side can be used as a specimen for biopsy. The collected tissue specimen has the largest size that can be expected from the given diameter of the outer needle tube. Hence, an adequate amount of the tissue specimen can be easily collected without increasing the diameter of the outer needle tube.

In addition, since the tissue specimen can be cut off by simply sliding the inner needle tube within the outer needle tube, only small sliding resistance develops and the cutting operation can be done efficiently.

In a preferred embodiment, an endoscopic tissue collecting instrument comprises an outer needle tube with a tip pointed forward that has a tissue aspirating port formed as an opening in the lateral side of an area close to the tip, an inner needle tube that is passed through the outer needle tube to be capable of moving back and forth and which has a blade formed at the distal end to cut off the tissue that has entered the tissue aspirating port, and an aspiration channel that communicates with the tissue aspirating port at the distal end and which extends to the basal ends of the outer and inner needle tubes.

If desired, the aspiration channel may be formed of the inner needle tube per se. The tissue aspirating port may be a cutout formed in the lateral side of the outer needle tube. The blade may be an annular one that is formed on the outer circumference of the inner needle tube.

The endoscopic tissue collecting instrument may be furnished with a guide tube through which the outer needle tube is passed to be capable of moving back and forth along the longitudinal axis.

According to the present invention, the basal end portion of a needle shaft is in engagement with the basal end portion of an outer sheath and a fixing member is provided that can be securely connected to or disconnected from the entrance of a treatment instrument insertion channel in an endoscope. Because of this design, the tissue specimen can be cut off by moving the outer sheath while the needle shaft that has been pierced into the tissue is securely connected to an endoscope. As a result, even in the case where the endoscopic tissue collecting instrument of the invention is passed into a tortuous treatment instrument insertion channel in a soft endoscope, the needle shaft and the outer sheath can be manipulated to move back and forth in small increments and independently of each other. Hence, the tissue collecting instrument of the invention is suitable for use with both a rigid and a soft endoscope and yet it can collect the tissue specimen in a safe and quick manner.

In a preferred embodiment, an endoscopic tissue collecting instrument comprises a needle shaft with a tip pointed forward that has a tissue retaining recess formed in the lateral side of an area close to the tip and an outer sheath that is fitted over the needle shaft to be capable of moving back and forth and which has a blade formed at the distal end to cut off the tissue retained in the recess. The basal end portion of the needle shaft is in engagement with the basal end portion of the outer sheath. A fixing member is provided, which can be securely connected to or disconnected from the entrance of a treatment instrument insertion channel in an endoscope.

The needle shaft and the outer sheath may each have flexibility. Preferably, the distal end of the needle shaft projects by a predetermined length from the exit of the treatment instrument insertion channel when the basal end portion of the needle shaft is brought into engagement with the fixing member and the fixing member is securely connected to the entrance of the treatment instrument insertion channel.

If desired, the basal end portion of the outer sheath may be capable of coming into or out of engagement with the fixing member independently of the needle shaft. The fixing member may be furnished with an urging member that pushes the outer sheath along the longitudinal axis so that the outer sheath is pushed along the longitudinal axis by the urging member if the outer sheath is brought out of engagement with the fixing member.

If desired, the area of engagement between the needle shaft and the outer sheath may be such that it can be securely connected to or disconnected from that part of the fixing member which is to be securely connected to the entrance of the treatment instrument insertion channel so that when said area is disconnected, the needle shaft and the outer sheath can be moved back and forth as an integral unit along the longitudinal axis. The endoscopic tissue collecting instrument maybe furnished with an aspiration channel that communicates with the tissue retaining recess in the distal end portion and which extends to the basal end portion of the needle shaft.

The present disclosure relates to the subject matter contained in Japanese patent application Nos. Hei. 11-290445 (filed on Oct. 13, 1999), Hei. 11-299007 (filed on Oct. 21, 1999) and Hei. 11-306298 (filed on Oct. 28, 1999), which are expressly incorporated herein by reference in their entireties.

DESCRIPTION OF THE PREFERRED EMBODIMENT

Embodiments of the present invention are described below with reference to accompanying drawings.

Figure 1:
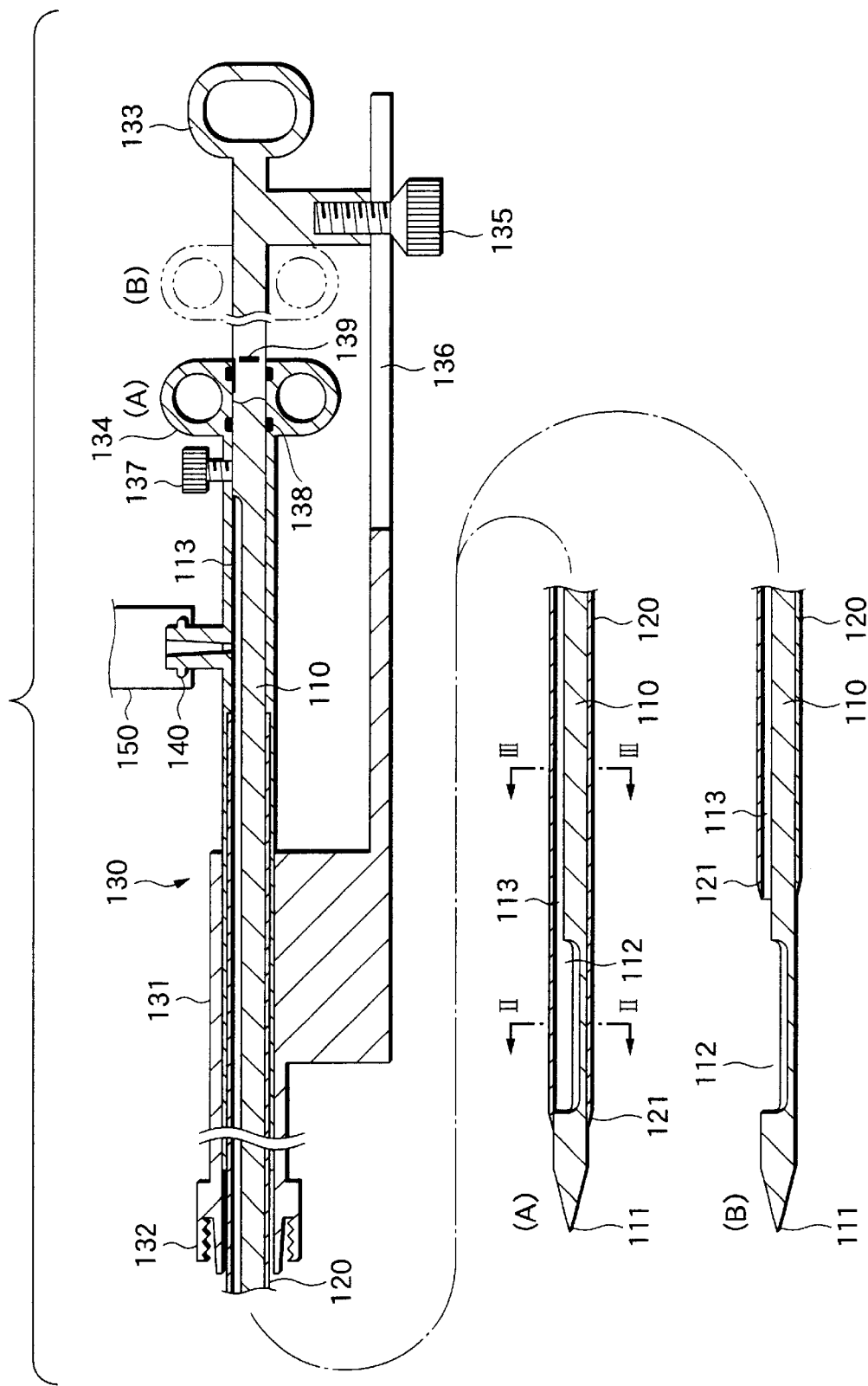
FIG. 1 is a longitudinal section showing the general layout of an endoscopic tissue collecting instrument according to a first embodiment of the invention.

FIG. 1 shows the general layout of an endoscopic tissue collecting instrument according to a first embodiment of the invention, with a cannula or outer sheath 120 being pushed to the predetermined foremost position (see under A) or pulled toward the operator (see under B).

Figure 2:
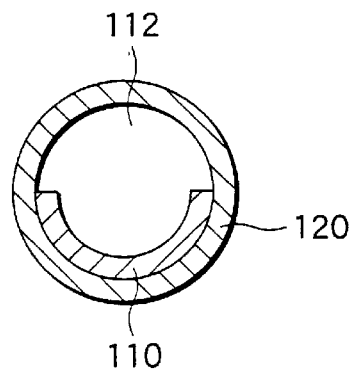
FIG. 2 is section II—II of FIG. 1.

A needle shaft 110 of a circular cross-sectional shape has a solid tip 111 formed at the distal end such that it is pointed forward. A recess 112 for retaining a collected tissue is formed in the lateral side of the needle shaft 110 in an area immediately behind the needle tip 111. FIG. 2 is section II—II of FIG. 1 and shows that the bottom of the recess 112 forms an arc of a circle concentric with the circumference of the needle shaft 110; this is in order to secure both volume and strength.

The outer sheath 120 is fitted over the needle shaft 110 by a distance generally equal to the entire length of the latter so that it is capable of moving back and forth along the longitudinal axis. The distal end portion of the outer sheath 120 is tapered such that an annular blade 121 is formed on the inner circumference of the outer sheath 120 at its distal end.

Figure 3:
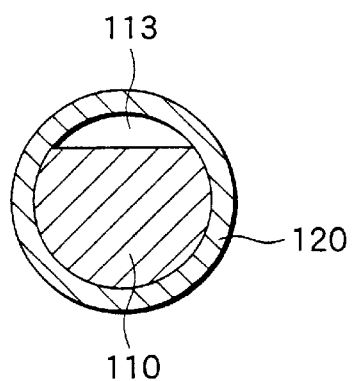
FIG. 3 is section of III—III of FIG. 1.

Formed in the space between the needle shaft 110 and the outer sheath 120 is an aspiration channel 113 that communicates with the tissue collecting recess 112 from the rear side and which extends over the entire length of that portion of the needle shaft 110 which is behind the recess 112. FIG. 3 is section III—III of FIG. 1 and shows that the as aspiration channel 113. The aspiration channel 113 is formed by cutting one side of the outer surface of the needle shaft 110 of a circular cross-sectional shape to produce a flat plane.

A manipulating section 130 provided close to the operator is furnished with a support body 131 that is to be attached to the treatment instrument insertion port of an endoscope with, for example, a Luer-Lock socket 132, and the needle shaft 110 and the outer sheath 120 are supported on the support body 131 in such a way that they are both capable of moving back and forth along the longitudinal axis.

A pull ring 133 is formed as an integral part of the end of the needle shaft 110 that is closer to the operator, and another pull ring 134 is formed as an integral part of the end of the outer sheath 120 that is closer to the operator. By sliding the pull rings 133 and 134 relative to each other, the distal end of the outer sheath 120 slides with respect to that of the needle shaft 110 as shown under A and B in FIG. 1.

It should be noted here that by tightening a manual, relatively locking screw 137, independent motions of the needle shaft 110 and the outer sheath 120 can be inhibited at any time so that they will move as an integral unit. Indicated by 138 is an O-ring seal.

By tightening a manual, needle shaft locking screw 135, the needle shaft 110 is fixed to the support body 131; if loosened, the locking screw 135 becomes freely movable along a slot 136 so that the needle shaft 110 is capable of moving back and forth along the longitudinal axis.

An index 139 is provided around an area of the needle shaft 110 that is closer to the operator; by seeing how far the index 139 is from the end face of the outer sheath 120 which is closer to the operator (namely, the end face of the pull ring 134), the operator can determine which portion of the needle shaft 110 the distal end of the outer sheath 120 is located at.

In the embodiment under consideration, the index 139 is provided in such a way as to tell the operator that the outer sheath 120 is in the position shown under A in FIG. 1 where it closes the tissue retaining recess 12 but does not project beyond the needle tip 11. Alternatively, the index may be provided to tell the operator that the outer sheath 120 is in the position shown under B in FIG. 1 or otherwise that the needle tip 111 has been pulled into the outer sheath 120.

A coupling socket 140 which can be connected to or disconnected from an aspirating device 150 is formed to project from the basal end of the outer sheath 120 which is closer to the operator. The coupling socket 140 communicates directly with the aspiration channel 113, and by applying suction through the aspirating device 150 such as a syringe that is connected to the socket 140, negative pressure is created in the tissue retaining recess 112 at the distal end of the needle shaft 110 and vacuum is drawn via the aspiration channel 113.

The endoscopic tissue collecting instrument thus constructed according to the embodiment under consideration is put to service after being inserted into the treatment instrument insertion channel of an endoscope, an ultrasonic endoscope and so forth. Note that in order to prevent the needle tip 111 from damaging the treatment instrument insertion channel while it is being inserted into or removed from the latter, the endoscopic tissue collecting instrument of the invention may first be passed through a guide tube typically made of a tetrafluoroethylene resin.

Figure 4:
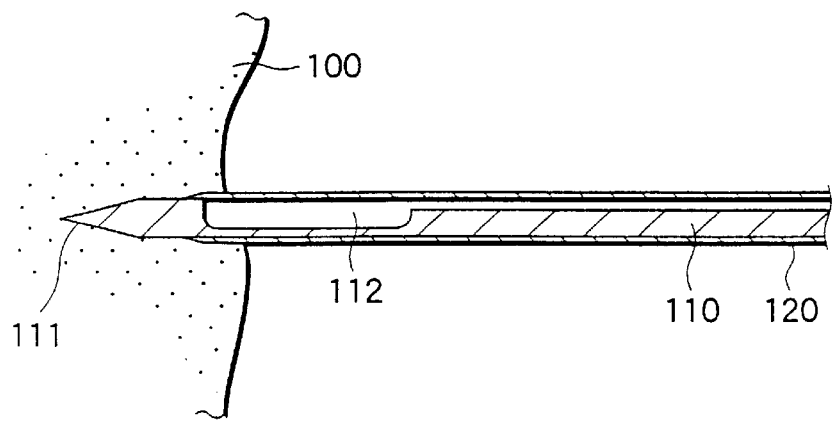
FIG. 4 is a longitudinal section showing the distal end portion of the endoscopic tissue collecting instrument as it is in the first phase of use.

FIGS. 4–7 show how a tissue specimen for biopsy is collected from the liver, the pancreas or other organ by means of the endoscopic tissue collecting instrument according to the embodiment described above. First, as shown in FIG. 4, the distal end of the outer sheath 120 is set near the distal end of the needle shaft 110 so that the tissue retaining recess 12 is closed with the outer sheath 120; the relatively locking screw 137 is tightened so that the needle shaft 110 becomes integral with the outer sheath 120; then, the needle shaft locking screw 135 is loosened and the needle tip 111 is pierced into the tissue 100.

Figure 5:
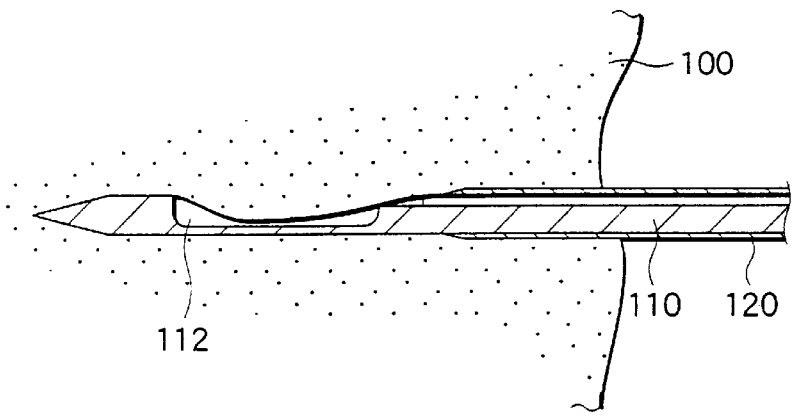
FIG. 5 is a longitudinal section showing the distal end portion of the endoscopic tissue collecting instrument as it is in the second phase of use.

When the tissue retaining recess 112 has reached a predetermined position in the tissue, the needle shaft locking screw 135 is tightened so that the needle shaft 110 is fixed to the support body 131; then, the relatively locking screw 137 is loosened and the outer sheath 120 is pulled toward the operator until the tissue retaining recess 112 becomes exposed as shown in FIG. 5, whereupon the tissue 100 gets into the recess 112.

Figure 6:
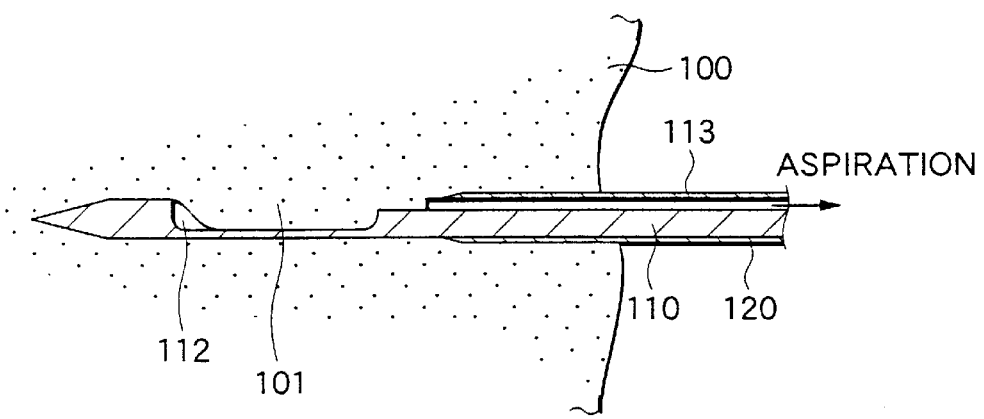
FIG. 6 is a longitudinal section showing the distal end portion of the endoscopic tissue collecting instrument as it is in the third phase of use.

Subsequently, the aspirating device 150 is activated and vacuum is drawn from the recess 112 via the aspiration channel 113; as shown in FIG. 6, the tissue specimen 101 which is a portion of the tissue 100 is then aspirated into the recess 112.

Figure 7:
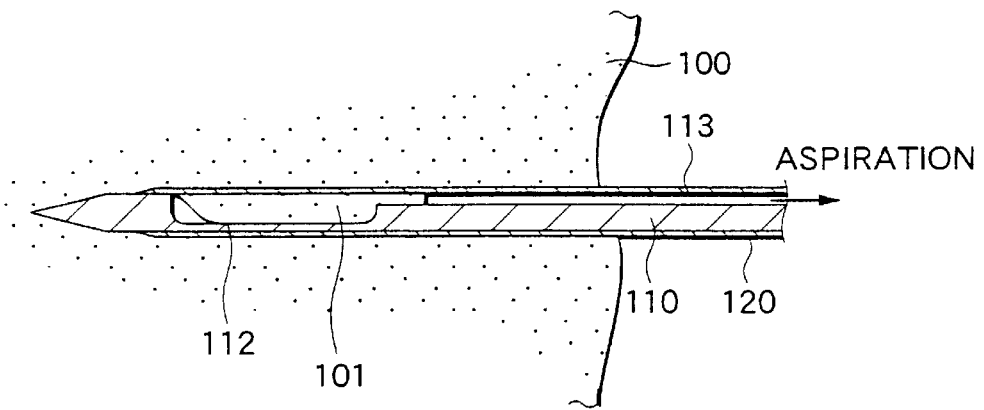
FIG. 7 is a longitudinal section showing the distal end portion of the endoscopic tissue collecting instrument as it is in the fourth phase of use.

As soon as this state is obtained, the outer sheath 120 is pushed forward to the initial position shown in FIG. 7, whereupon the tissue specimen 101 being sucked to the bottom of the recess 112 is severed from the rest of the tissue 100 with the blade 121 of the outer sheath 120 and retained within the recess 112.

Thus, the tissue specimen 101 of an adequate size can be easily collected. As a further advantage, since the entire length of the aspiration channel 113 is exposed on the surface of the needle shaft 110, not only the formation of the aspiration channel but also the cleaning and disinfection of it after service can be accomplished with relative ease.

Figure 8:
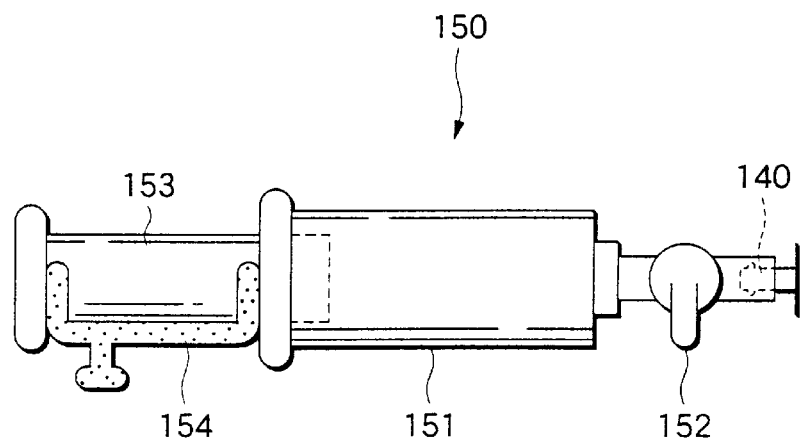
FIG. 8 is a side view showing an example of the aspirating device that may be used with the endoscopic tissue collecting instrument of the invention.

FIG. 8 shows an example of he aspirating device 150 which is suitable for use with the endoscopic tissue collecting instrument according to the first embodiment of the invention. The barrel of a syringe 151 is connected to the coupling socket 140 via a cock 152 and negative pressure is created in the barrel 151 by pulling a plunger 153. Indicated by 154 is a detachable spacer that is fitted on the plunger in the pulled state so as to maintain the negative pressure in the barrel 151.

Figure 9:
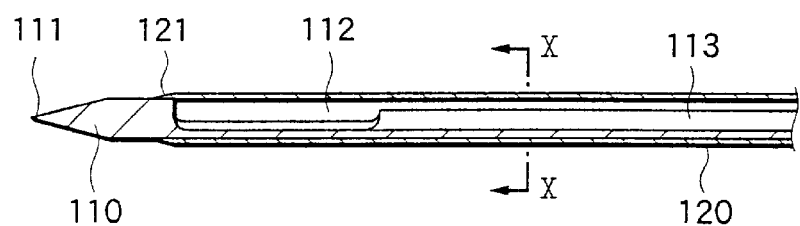
FIG. 9 is a longitudinal section showing the distal end portion of an endoscopic tissue collecting instrument according to a second embodiment of the invention.
Figure 10:
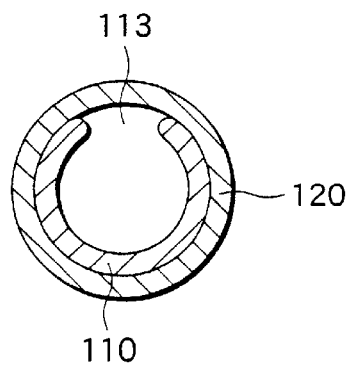
FIG. 10 is section X—X of FIG. 9.

FIG. 9 shows the distal end portion of an endoscopic tissue collecting instrument according to a second embodiment of the invention. As shown in FIG. 10 which is section X—X of FIG. 9, the aspiration channel 113 is shaped to have a cross section in an inverted Ω form. That is, the aspiration channel 113 has a hollow internal core extending on and along the longitudinal axis thereof.

This is an effective way to increase the cross-sectional area of the aspiration channel 113 by a sufficient degree to have a greater amount of vacuum drawn from the tissue retaining recess 112. As a further advantage, the needle shaft 110 which is in pipe form has increased flexibility and can be easily passed through the treatment instrument insertion channel of a soft (flexible) endoscope.

Figure 11:
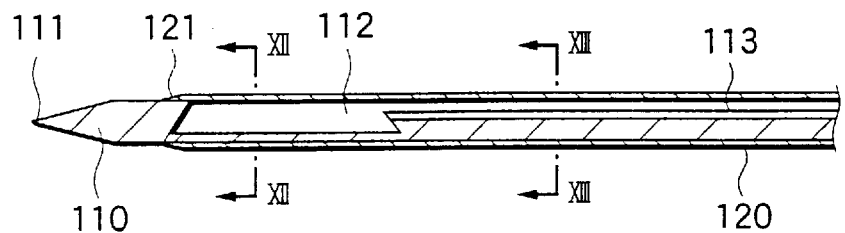
FIG. 11 is a longitudinal section showing the distal end portion of an endoscopic tissue collecting instrument according to a third embodiment of the invention.

FIG. 11 shows the distal end portion of an endoscopic tissue collecting instrument according to a third embodiment of the invention. The tissue retaining recess 112 flares inwardly in such a way that the walls at the front and rear ends are inclined to depart from each other with increasing depth. With this design, the tissue specimen 101 being cut off with the outer sheath 120 can be prevented from lifting from the tissue retaining recess 112, thus making it possible to collect the tissue specimen 101 of a larger size.

Figure 12:
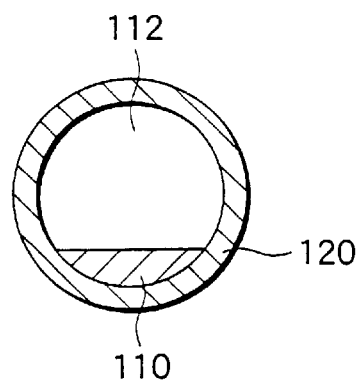
FIG. 12 is section XII—XII of FIG. 11.
Figure 13:
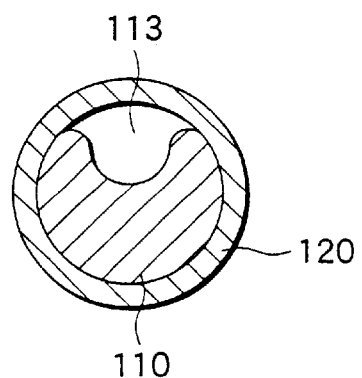
FIG. 13 is section XIII—XIII of FIG. 11.

In the third embodiment described above, the bottom of the tissue retaining recess 112 is formed as a flat plane (see FIG. 12 which is section XII—XII of FIG. 11) and the aspiration channel 113 is formed as a groove with a curved cross section (see FIG. 13 which is section XIII—XIII of FIG. 11). The endoscopic tissue collecting instrument of the invention can be modified in various ways as exemplified above.

Figure 14:
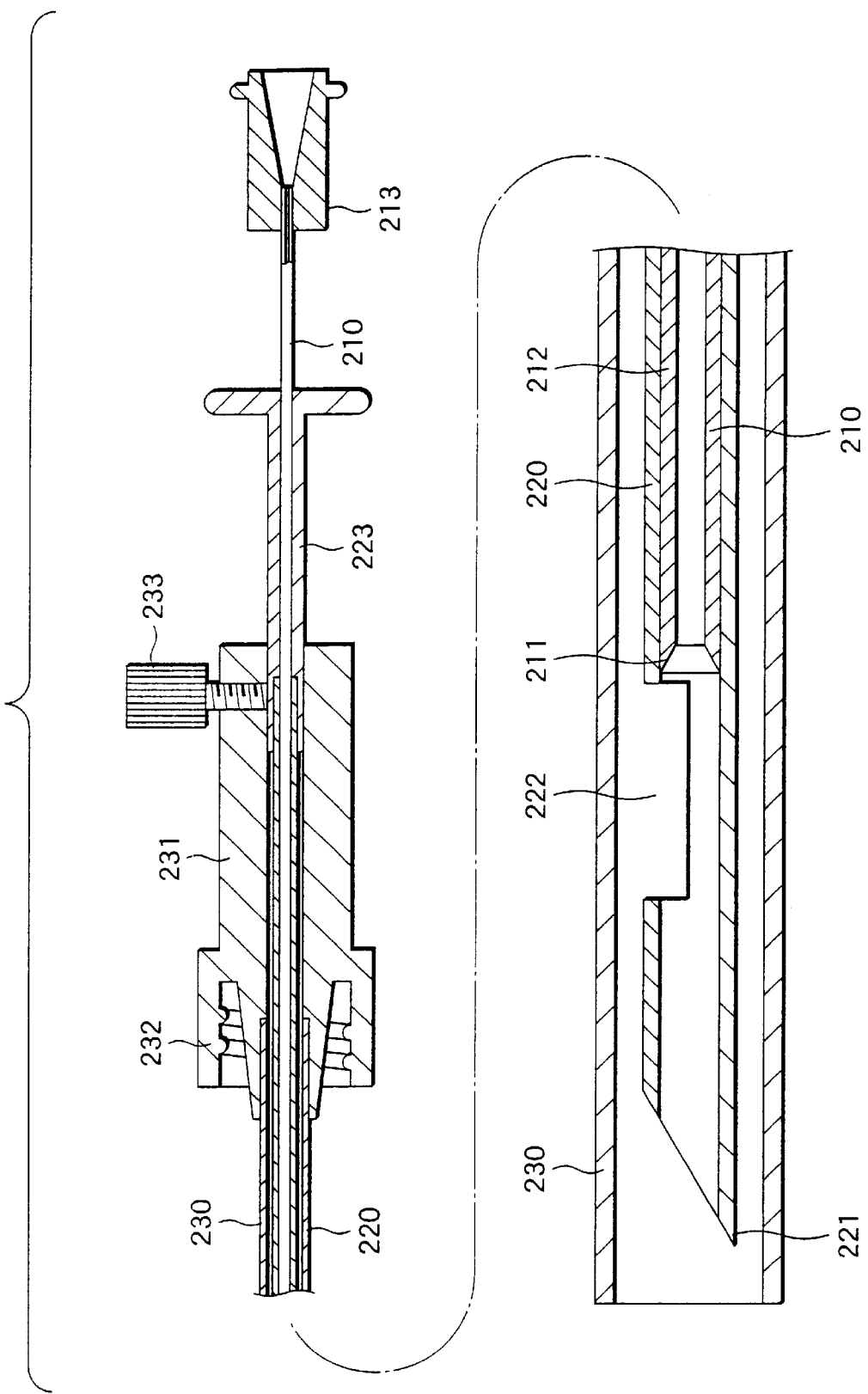
FIG. 14 is a longitudinal section showing the general layout of an endoscopic tissue collecting instrument according to a fourth embodiment of the invention.

FIG. 14 shows the genera layout of an endoscopic tissue collecting instrument according to a fourth embodiment of the invention. An outer needle tube 220 formed as a round pipe having a constant diameter throughout its length has a needle tip 221 formed at the distal end that is cut at an angle as in the case of a syringe so that it is sharply pointed forward.

A port 222 through which the tissue is to be aspirated inward is formed in the lateral side of the outer needle tube 220 in an area immediately behind the needle tip 221. The tissue aspirating port 222 is formed by making a cutout in the lateral side of the outer needle tube 220 in pipe form to a depth almost equal to its radius.

An inner needle tube 210 in round pipe form has an annular blade 211 formed on the outer circumference of the distal end thereof. The inner needle tube 210 is passed into the outer needle tube 220 over a distance substantially equal to its length so that it is capable of moving back and forth along the longitudinal axis. The operator manipulates the inner needle tube 210 to move it forward so that the blade 211 passes over the tissue aspirating port 222.

If the endoscopic tissue collecting instrument is to be used with a rigid endoscope, both the outer needle tube 220 and the inner needle tube 210 are formed of a metal pipe; if it is to be used with a soft endoscope having a flexible part to be inserted into a body cavity, the two needle tubes maybe formed of a flexible plastic material or a metal pipe (e.g. a stainless steel pipe) that is sufficiently thin-walled to have flexibility.

If a thin-walled stainless steel pipe is used, the outer needle tube 220 may be sized to have an outside diameter of about 1.0 mm and an inside diameter of about 0.9 mm whereas the inner needle tube 210 may be sized to have an outside diameter of about 0.9 mm and an inside diameter of about 0.8 mm; with these dimensions, both needle tubes can be bent with sufficient suppleness to permit use with a soft endoscope.

The inner needle tube 210 extends farther beyond the basal end of the outer needle tube 220 toward the operator, and its basal end is fitted with a suction line socket 213 for establishing connection to an aspirating device such as a syringe. Thus, by applying suction to the socket 213, vacuum can be drawn from the tissue aspirating port 222 via an aspiration channel 212 defined by the bore of the inner needle tube 210.

A grip 223 attached to the basal end of the outer needle tube 220 is made of a rigid material. By holding the grip 223 between the finger and thumb, the operator not only manipulates the inner needle tube 210 to move it back and forth relative to the outer needle tube 220 but also manipulates the outer needle tube 220 relative to the treatment instrument insertion channel of an endoscope as will be described later.

Indicated by 230 is a guide tube that protects the treatment instrument insertion channel of a soft endoscope from being damaged by the needle tip 221 while the endoscopic tissue collecting instrument is inserted into or removed from the insertion channel. The guide tube is typically made of a tetrafluoroethylene resin.

A support member 231 is securely coupled to the basal end of the guide tube 230, and it has a mount socket 232 with a female thread for establishing firm coupling to the treatment instrument insertion port of the endoscope The support member 231 is also furnished with a manual locking screw 233 that is capable of fixing the grip 223 in a desired position.

Figure 15:
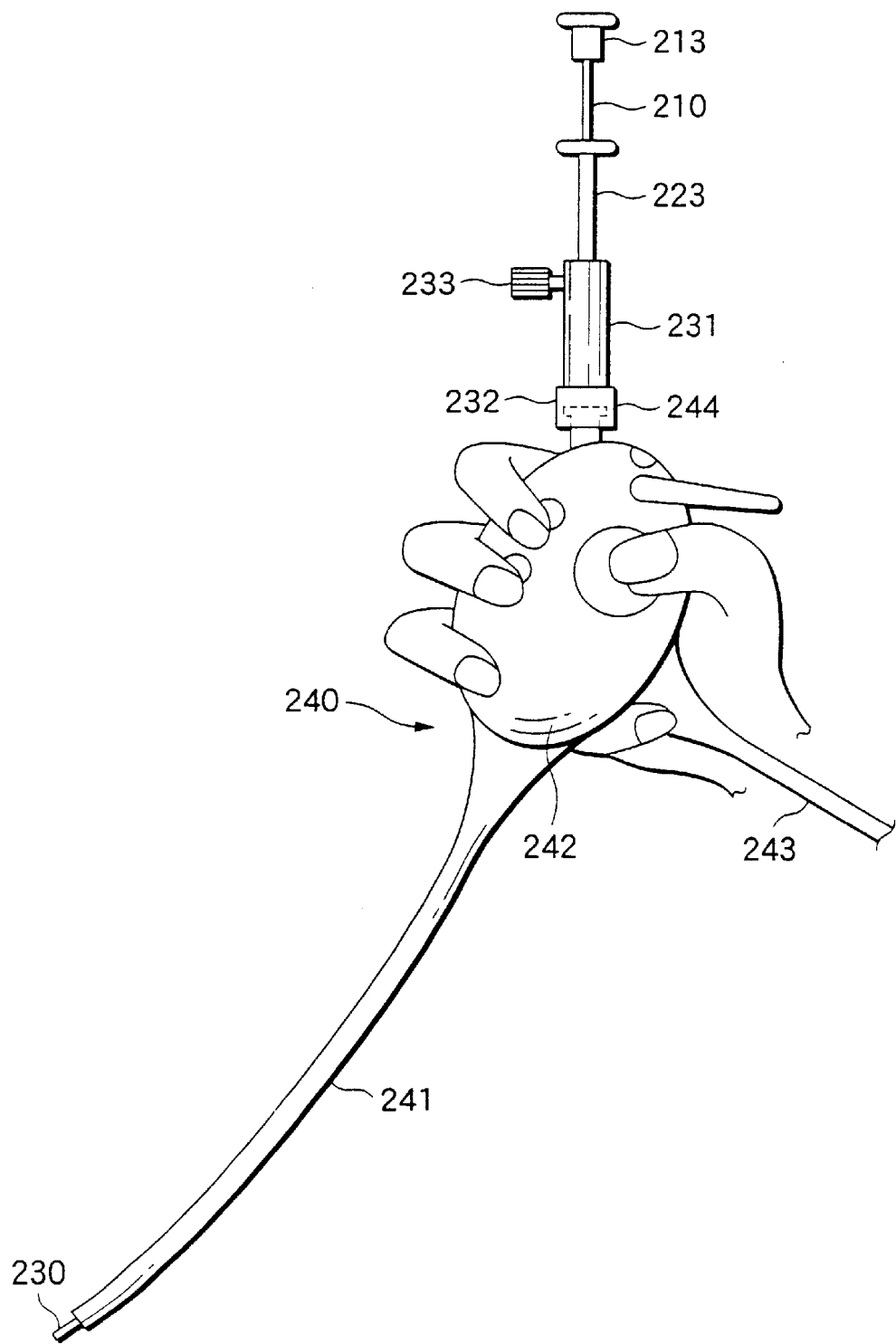
FIG. 15 is an exterior view showing how the endoscopic tissue collecting instrument is used as an attachment to a soft endoscope.

FIG. 15 shows the endoscopic tissue collecting instrument as it has been set on a soft endoscope 240. Reference numeral 241 designates the part which is encased in a flexible tube and which is to be inserted into a body cavity; 242 is the manipulating section; 243 is a connector to a video processor and light source unit; 244 is the treatment instrument insertion port.

With the locking screw 233 held in a tightened position, the guide tube 230 is passed into the treatment instrument insertion channel of the endoscope and the mount socket 232 is held in engagement with the treatment instrument inlet 244.

Subsequently, the operator manipulates the inner needle tube 210 to move it back and forth. If the locking screw 233 is loosened and the operator manipulates the grip 223 to move it back and forth, the outer needle tube 220 can be moved back and forth together with the inner needle tube 210.

Figure 16:
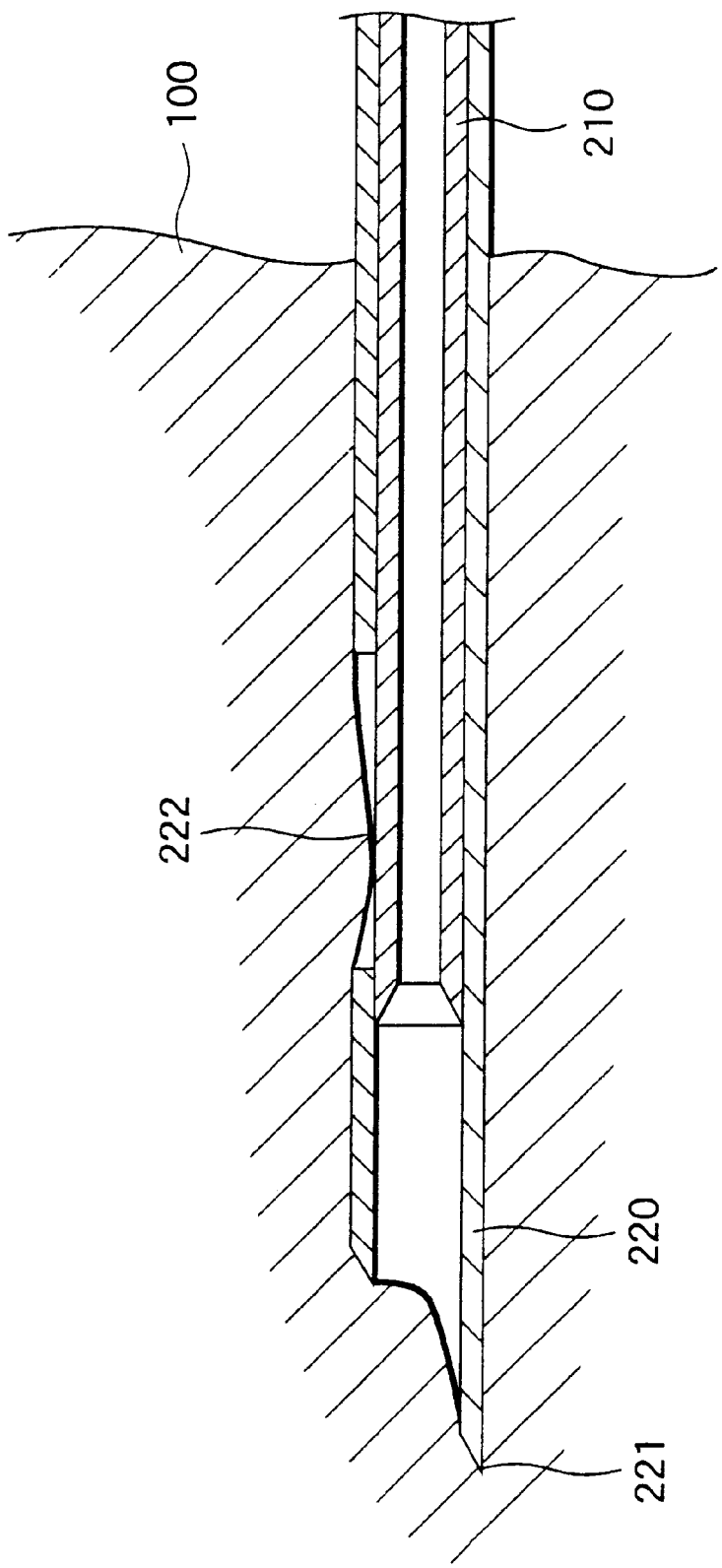
FIG. 16 is a longitudinal section showing the distal end portion of the endoscopic tissue collecting instrument as it is in the first phase of use.
Figure 17:
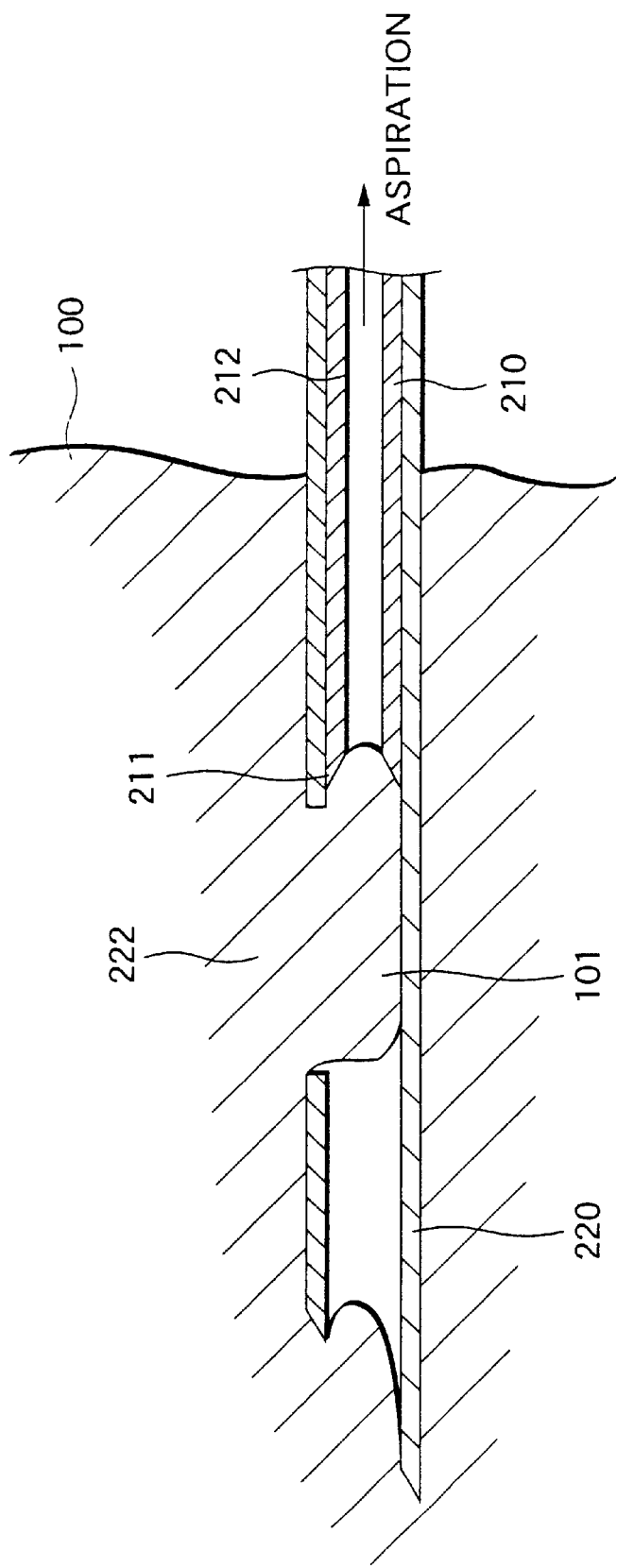
FIG. 17 is a longitudinal section showing the distal end portion of the endoscopic tissue collecting instrument as it is in the second phase of use.
Figure 18:
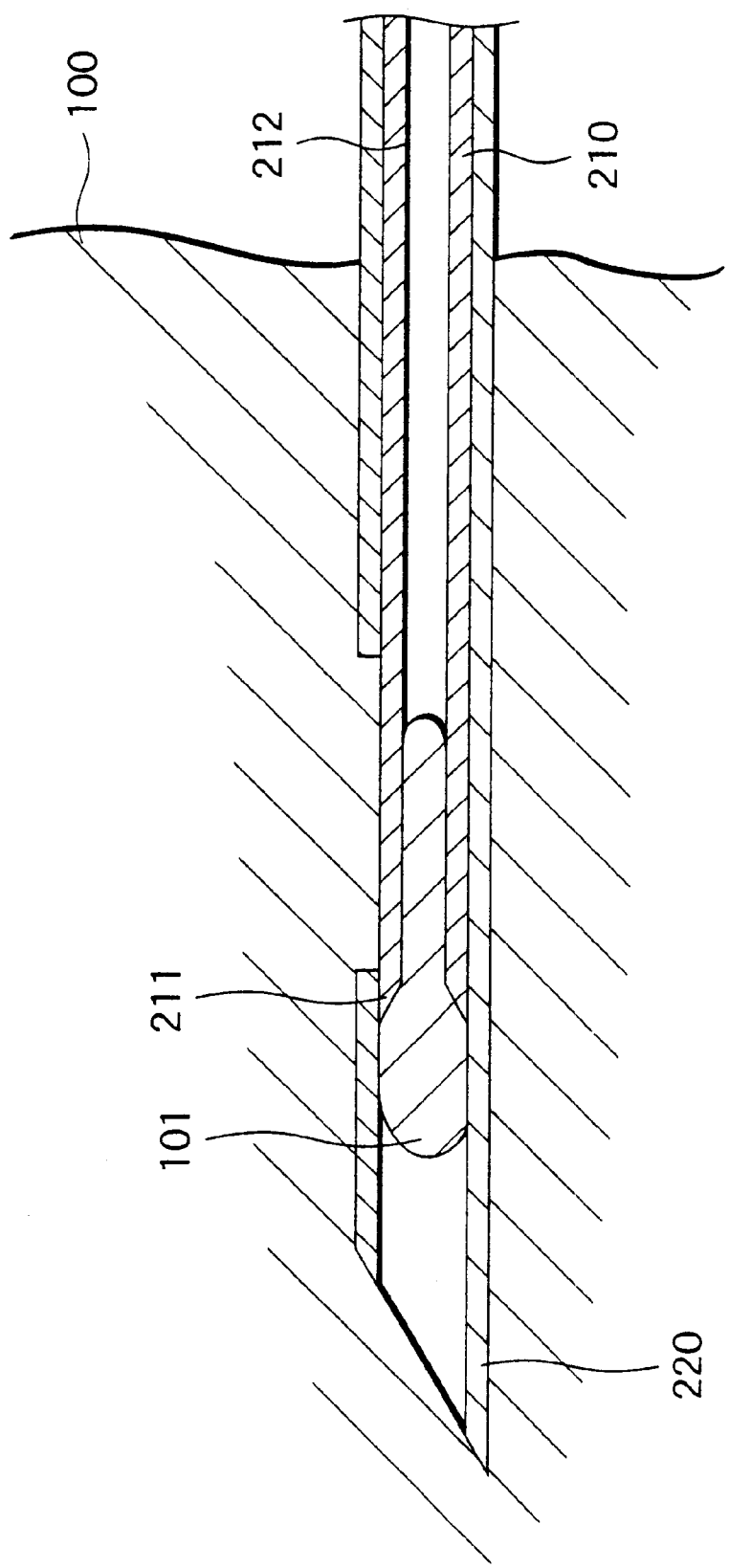
FIG. 18 is a longitudinal section showing the distal end portion of the endoscopic tissue collecting instrument as it is in the third phase of use.

FIGS. 16 to 18 show how a tissue specimen for biopsy is collected from the liver, the pancreas or other organ by means of the endoscopic tissue collecting instrument according to the fourth embodiment described above. First, as shown in FIG. 16, the tissue aspirating port 222 is closed with the inner needle tube 210 and the tip 221 of the outer needle tube 220 is pierced into the tissue 100.

When the tissue aspirating port 222 has reached a predetermined position in the tissue, the inner needle tube 210 is pulled toward the operator until the tissue aspirating port 222 becomes exposed and vacuum is drawn toward the operator via the aspiration channel 212 as shown in FIG. 17.

Then, the tissue specimen 101 which is a portion of the tissue 100 is aspirated into the outer needle tube 220 via the tissue aspirating port 222. Some part of the tissue specimen 101 goes farther into the aspiration channel 212 in the inner needle tube 210 to reach an area in the neighborhood of its entrance.

As will be described in the following paragraph, all the tissue 100 that has been aspirated via the tissue aspirating port 222 is collected as the tissue specimen 101. Hence, the thickness of the collected tissue specimen is exactly the same as the inside diameter of the outer needle tube 220 and it is the largest size that can be secured with the given diameter of the outer needle tube 220.

In the next step, with the tissue specimen 101 having been aspirated, the inner needle tube 210 is pushed forward as shown in FIG. 18, whereupon the tissue specimen 101 is cut off from the rest of the tissue 100 by the blade 211 of the inner needle tube 210 which slides along the inner surface of the outer needle tube 220 and the severed tissue specimen 101 is retained in the tissue aspirating port 222.

In this way, the tissue specimen 101 of a large size can be easily collected. Since the inner needle tube 210 slides within the outer needle tube 220, it receives a small enough sliding resistance to be smoothly pushed forward. As is clear from FIG. 18, some part of the tissue specimen 101 is slightly compressed and reaches into the inner needle tube 210.

Figure 19:
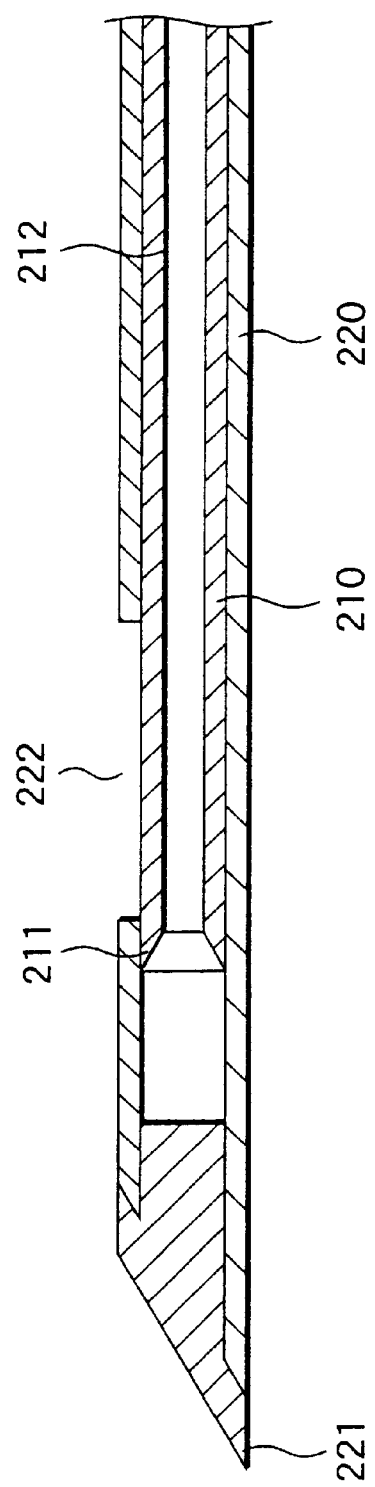
FIG. 19 is a longitudinal section showing the distal end portion of an endoscopic tissue collecting instrument, which is a modification of the fourth embodiment.

The present invention is by no means limited to the embodiments described above and various modifications can be made. For example, the aspiration channel 212 in the fourth embodiment may be formed in other areas than the bore of the inner needle tube 210, such as the boundary between the inner needle tube 210 and the outer needle tube 220. If desired, the distal end portion of the outer needle tube 220 may be sealed as shown in FIG. 19.

Figure 20:
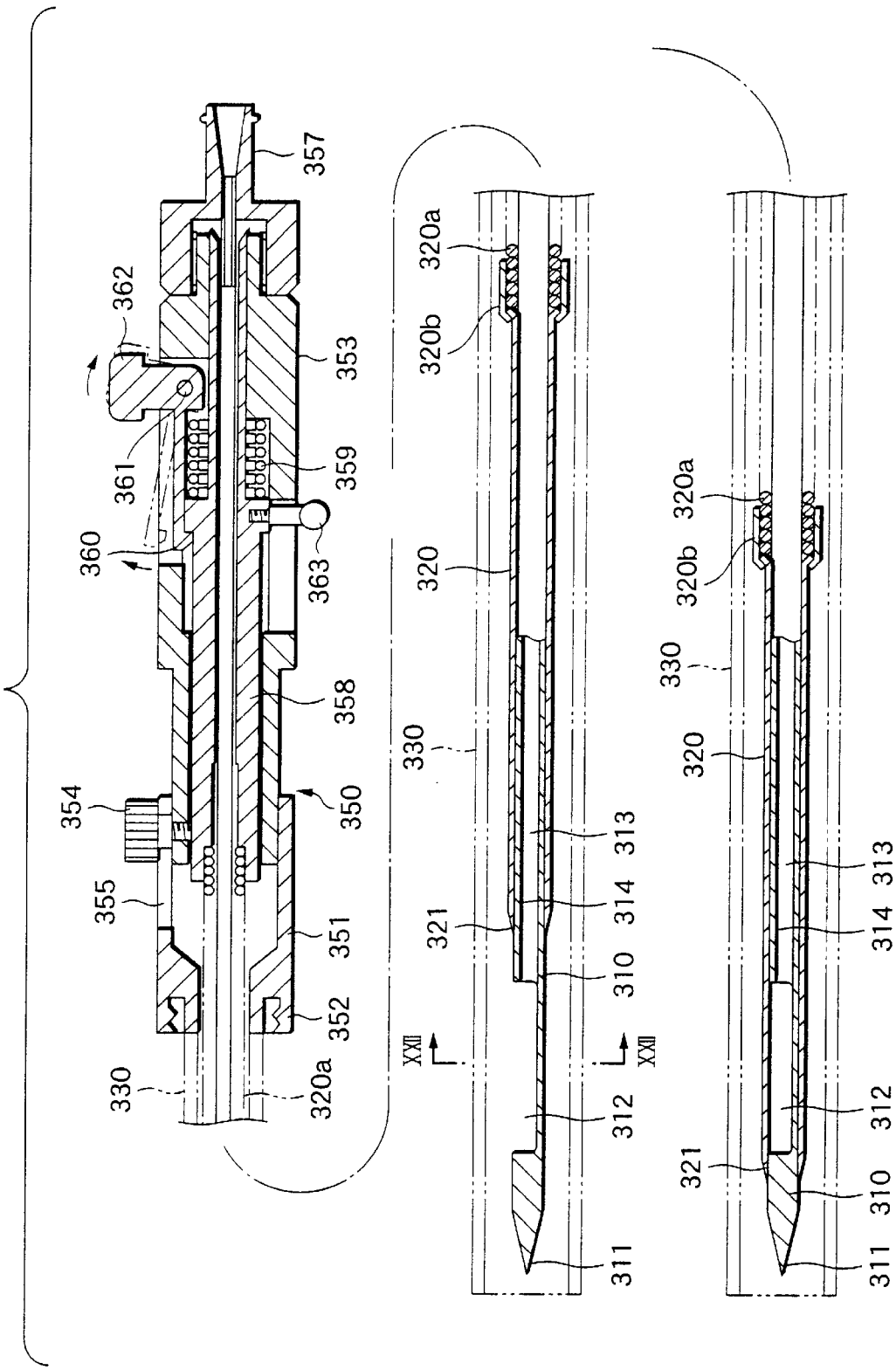
FIG. 20 is a longitudinal section showing the general layout of an endoscopic tissue collecting instrument according to a fifth embodiment of the invention.

FIG. 20 shows the general layout of an endoscopic tissue collecting instrument according to a fifth embodiment of the present invention, with its distal end portion being shown under A for the case where a cannula or outer sheath 320 has been pulled toward the operator and under B for the case where it has been pushed to the predetermined foremost position.

Figure 22:
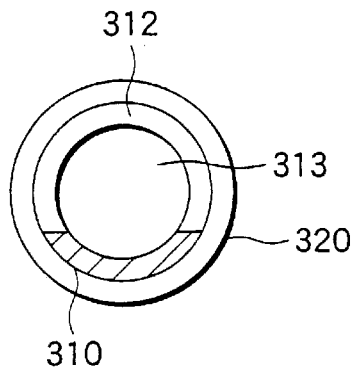
FIG. 22 is section of XXII—XXII of FIG. 20.

A needle shaft 310 has a solid tip 311 formed at the distal end such that it is pointed forward. A recess 312 for retaining a collected tissue is formed in an area immediately behind the needle tip 311. As is clear from FIG. 22 which is section XXII—XXII of FIG. 20, the recess 312 is formed by cutting out the lateral side of the needle shaft 310.

An aspiration channel 313 that communicates with the tissue retaining recess 312 is formed through the entire length of that part of the needle shaft 310 which is rearward of the recess 312. Hence, the part of the needle shaft 310 which is rearward of the recess 312 is in pipe form. The needle shaft 310 also has a groove 314 that is formed in a position a little behind the recess 312. A rod or the like may be inserted into the groove to push out a tissue specimen 101 collected in the recess 312 (described later).

The needle shaft 310 is typically formed of a flexible plastic material. Alternatively, it may be formed of a stainless steel or other metallic material if the portion which is in pipe form is sufficiently thin-walled that it is flexible enough to be passed through a soft endoscope.

The outer sheath 320 is fitted over the needle shaft 310 so that it is capable of moving back and forth along the longitudinal axis. The distal end portion of the outer sheath 320 which is formed as a thin-walled tube is tapered such that an annular blade 321 is formed on the inner circumference of the outer sheath 320 at its distal end.

All portion of the outer sheath 320 except the neighborhood of the distal end is formed of a coil pipe 320a wound in close turns to ensure that no great resistance will develop during insertion into or removal from a soft endoscope, and a coupling ring 320b is securely attached to the joint between the coil pipe 320a and the distal tubular portion of the outer sheath 320.

Indicated by 350 is a manipulating section (fixing member) provided at the end of the tissue collecting instrument that is closer to the operator. It comprises a generally cylindrical mount 351 and a mounting socket 352 that can be securely connected to or disconnected from the entrance of a treatment instrument insertion channel in an endoscope. The mounting socket 352 is typically formed as a Luer-Lock female socket.

A basal end retainer 353 is fitted into the mount 351 in such a way that it can be moved back and forth along the longitudinal axis; the two members can be securely connected to or disconnected from each other as desired by manually adjusting a locking screw 354. A slot 355 is formed in the mount 351 parallel to the longitudinal axis. Since the locking screw 354 extends through this slot to be threaded into the basal end retainer 353, the basal end retainer 353 can be moved back and forth relative to the mount 351 over the distance corresponding to the distance for which the locking screw 354 can be moved along the slot 355.

A suction line socket 357 to be connected to an aspirating device is detachably threaded into the end of the basal end retainer which is closer to the operator, and the basal end of the needle shaft 310 is securely connected to the suction line socket 357. Hence, by attaching an aspirating device to the suction line socket 357, vacuum can be drawn from the tissue retaining recess 312 via the aspiration channel 313 extending through the needle shaft 310.

When the suction line socket 357 has been threaded into the basal end retainer 353, the needle shaft 310 is in firm engagement with the basal end retainer 353. If the suction line socket 357 is disengaged from the basal end retainer 353, the needle shaft 310 becomes free to move back and forth along the longitudinal axis independently of the manipulating section 350.

A cannula retainer tube or outer sheath retainer tube 358 is provided inside the basal end retainer 353 in such a way that it can move back and forth along the longitudinal axis. The basal end portion of the coil pipe 320a of the outer sheath 320 is securely coupled to the distal end portion of the retainer tube 358. The needle shaft 310 is loosely passed through the axial opening of the retainer tube 358.

The retainer tube 358 is urged forward by a compressive coil spring 359, and with the spring 359 being in a compressed state, the retainer tube 358 is held in position by a hook 360 which is an integral part of a control knob 362 that is pivotal about a rotating shaft 361. The integral assembly of the hook 360 and the control knob 362 is attached to the basal end retainer 353.

Because of this design, when the endoscopic tissue collecting instrument is in the state shown in FIG. 20 where the outer sheath retainer tube 358 is held in position by the hook 360, the outer sheath 320 is pulled toward the operator and does not close the tissue retaining recess 312 as shown under A in FIG. 20.

If the control knob 362 is allowed to pivot in the direction indicated by the arrow so that the hook 360 disengages the outer sheath retainer tube 358, the tube 358 is pushed by the compressive coil spring 359 to move forward.

As a result, the outer sheath 320 is pushed to the predetermined foremost position and the blade 321 moves forward by sliding over the tissue retaining recess 312 to close it as shown under B in FIG. 20. Indicated by 363 is a return knob for bringing the outer sheath retainer tube 358 back to the position where it is in engagement with the hook 360.

If the endoscopic tissue collecting instrument according to the embodiment under discussion is to be used with a soft endoscope, a guide tube 330 typically made of a tetrafluoroethylene resin is coupled at the basal end to the mount 351 and both the needle shaft 310 and the outer sheath 320 are loosely passed into the guide tube 330 until their distal ends are covered by it; the endoscopic tissue collecting instrument thus enclosed in the guide tube is then passed into the treatment instrument insertion channel of the endoscope. In this way, the instrument can be used without letting the needle tip 311 damage the treatment instrument insertion channel.

If the outer sheath 320 is designed in such a way that it can be slid up to the position where its distal end covers the tip 311 of the needle shaft 310, there is no need to use the guide tube 330 and the tissue collecting instrument can be used with the soft endoscope without damaging its treatment instrument insertion channel.

Figure 21:
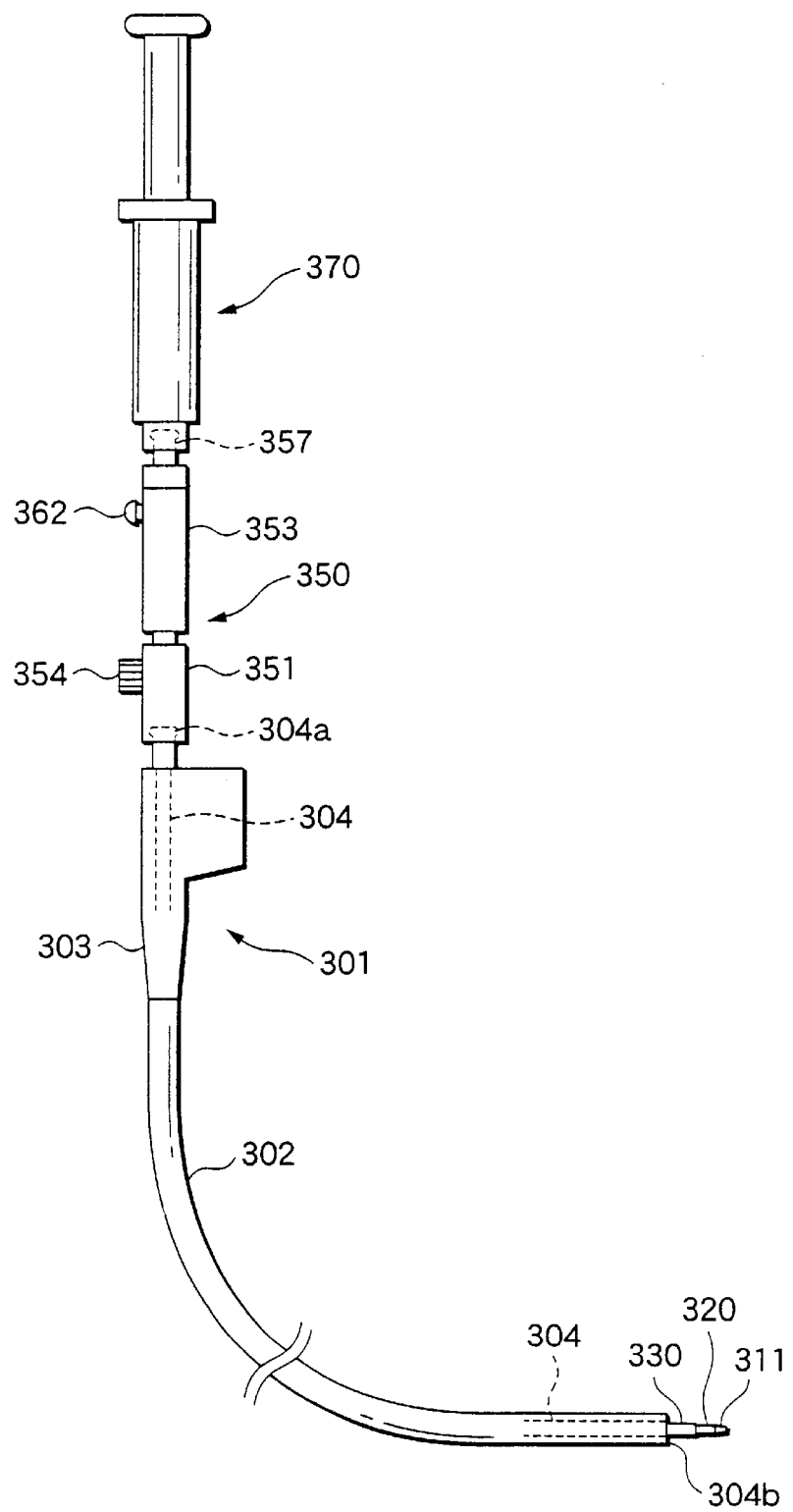
FIG. 21 is an exterior view showing how the endoscopic tissue collecting instrument is used as an attachment to a soft endoscope.

FIG. 21 shows how the endoscopic tissue collecting instrument according to the fifth embodiment under consideration is used as an attachment to the soft endoscope which is generally indicated by 301. Numeral 302 refers to the part which is encased in a flexible tube and which is inserted into a body cavity; 303 is the endoscope manipulating section; and 304 is the treatment instrument insertion channel.

The treatment instrument insertion channel 304 has an insertion socket 304a that projects from the endoscope manipulating section 303. With the mount 351 being attached to this socket, the distal end of the guide tube 330 (as well as the distal ends of the outer sheath 320 and the needle shaft 310) project by a predetermined length from the exit 304b of the channel 304 at the distal end of the part 302.

In FIG. 21, the locking screw 354 is tightened to such an extent that both the distal end of the outer sheath 320 and the tip 311 of the needle shaft 310 project from the distal end of the guide tube 330. The aspirating device 370 which is typically a syringe is attached to the suction line socket 357.

FIGS. 23–26 show how a tissue specimen for biopsy is collected from the liver, the pancreas or other organ by means of the endoscopic tissue collecting instrument according to the fifth embodiment described above. The guide tube 330 is not shown in those figures.

Figure 23:
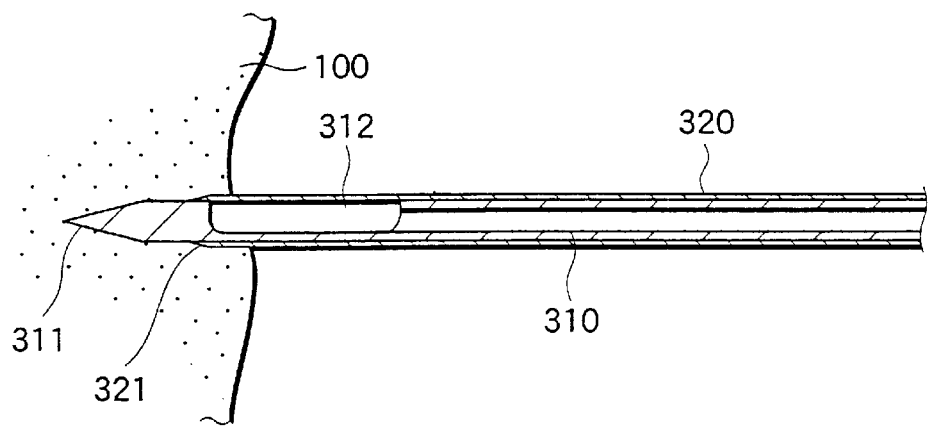
FIG. 23 is a longitudinal section showing the distal end portion of the endoscopic tissue collecting instrument as it is in the first phase of use.

First, the manipulating section 350 is left unconnected to the endoscope 301, and the hook 360 releases the outer sheath retainer tube 358 so that the tissue retaining recess 312 is closed with the distal end portion of the outer sheath 320. Then, both the needle shaft 310 and the outer sheath 320 are allowed to move together with the manipulating section 350, and the needle tip 311 projecting from the distal end of the inserted part 302 of the endoscope 301 is pierced into the tissue 100 as shown in FIG. 23.

Figure 24:
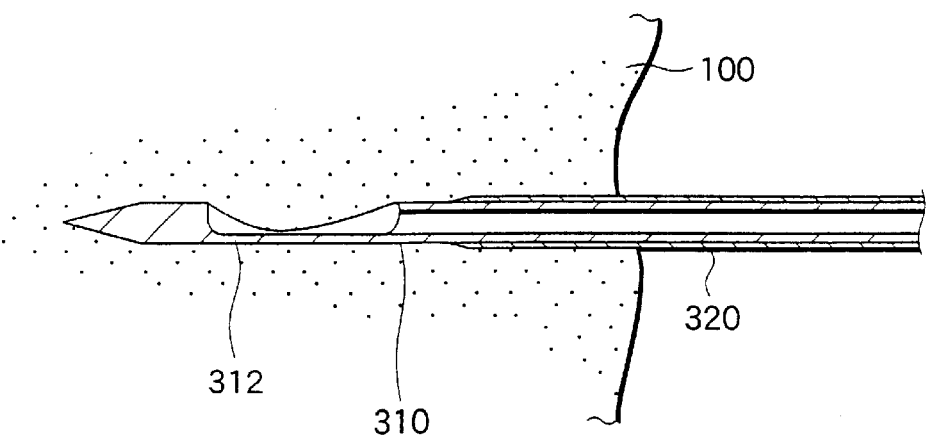
FIG. 24 is a longitudinal section showing the distal end portion of the endoscopic tissue collecting instrument as it is in the second phase of use.
Figure 25:
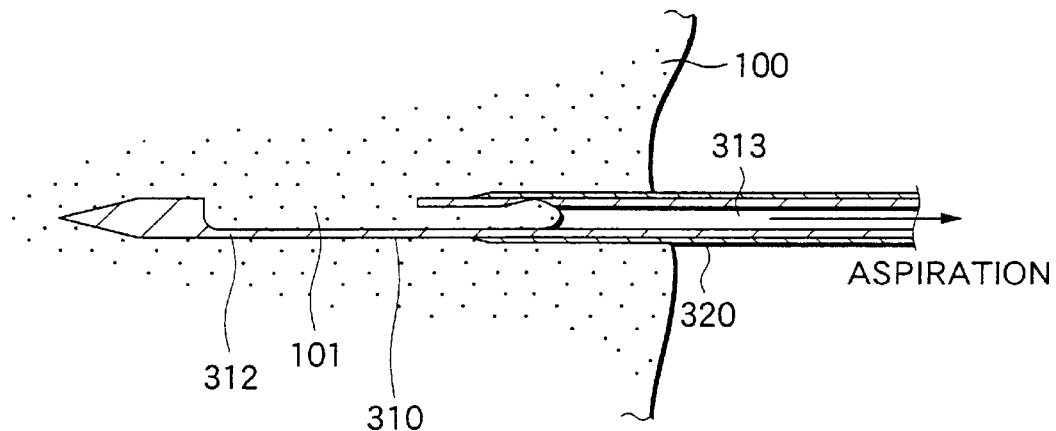
FIG. 25 is a longitudinal section showing the distal end portion of the endoscopic tissue collecting instrument as it is in the third phase of use.

When the needle tip 311 has been pierced by a predetermined length, the mount socket 352 is securely connected to the endoscope manipulating section 303 and the return knob 363 is pulled up so that the hook 360 engages the outer sheath retainer tube 358, whereupon the outer sheath 320 is pulled toward the operator and the tissue retaining recess 312 becomes exposed to receive a portion of the tissue 100 as shown in FIG. 24.

Then, the aspirating device 370 is activated and vacuum is drawn from the tissue retaining recess 312 via the aspiration channel 313, whereupon the tissue specimen 101 is sucked into the recess 312 and further inward to reach the area near the entrance of the aspiration channel 313.

Figure 26:
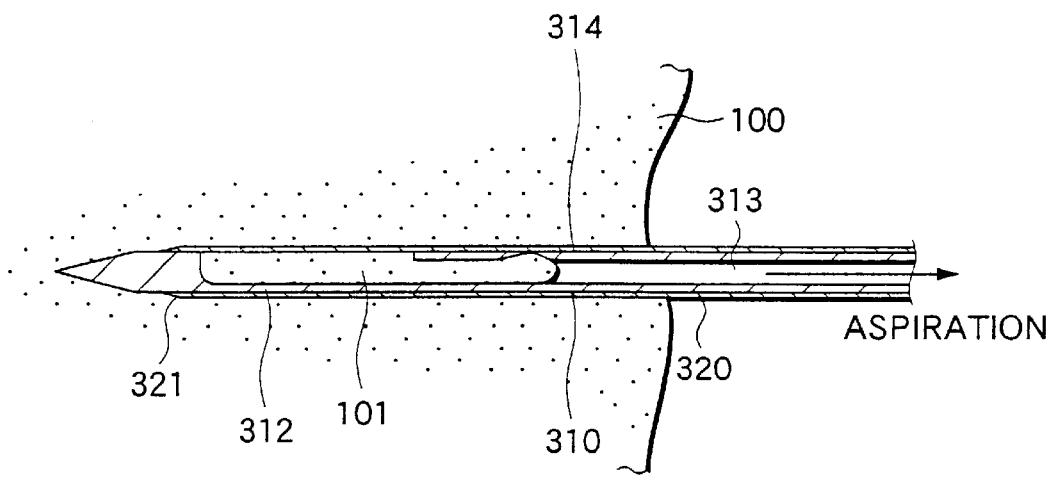
FIG. 26 is a longitudinal section showing the distal end portion of the endoscopic tissue collecting instrument as it is in the fourth phase of use.

As soon as this state is obtained, the control knob 362 is allowed to pivot, causing the hook 360 to release the outer sheath retainer tube 358; as shown in FIG. 26, the outer sheath 320 is immediately pushed forward and the tissue specimen 101 is severed from the rest of the tissue 100 with the blade 321 of the outer sheath 310 and retained in the recess 312.

Thus, the tissue specimen 101 of a larger volume than the tissue retaining recess 312 can be easily collected. To recover the collected tissue specimen, the needle shaft 310 is pulled out of the manipulating section 350 and a thin rod or the like is forced into the groove 14.

Figure 27:
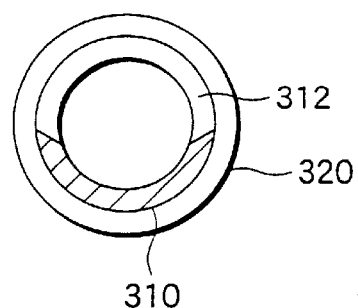
FIG. 27 is a cross section showing a variation of section XXII—XXII of FIG. 20.
Figure 28:
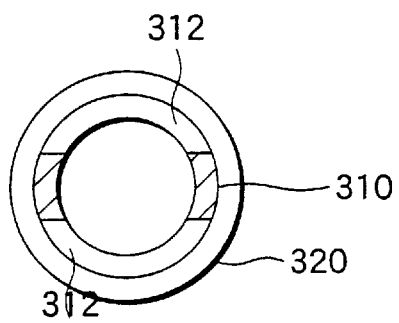
FIG. 28 is a cross section showing another variation of section XXII—XXII of FIG. 20.

The present invention is by no means limited to the embodiments described above and various modifications can be made. For example, the strength of the tissue retaining recess 12 can be enhanced by making a cutout to a depth which is about one half the radius of the needle shaft 310, as shown in FIG. 27. Alternatively, two cutouts may be formed from opposite sides as shown in FIG. 28.

Figure 29:
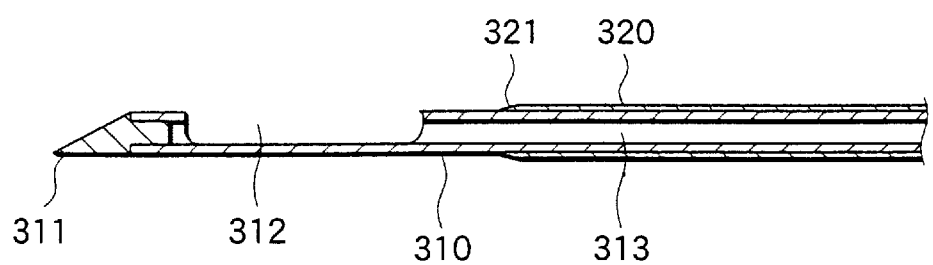
FIG. 29 is a longitudinal section showing a variation of the distal end portion of the endosopic tissue collecting instrument.
Figure 30:
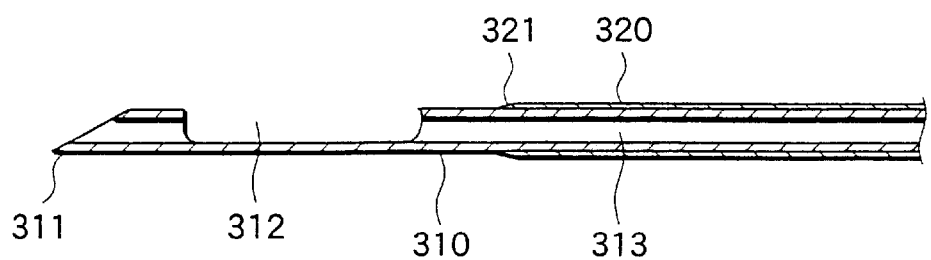
FIG. 30 is a longitudinal section showing another variation of the distal end portion of the endoscopic tissue collecting instrument.
Figure 31:
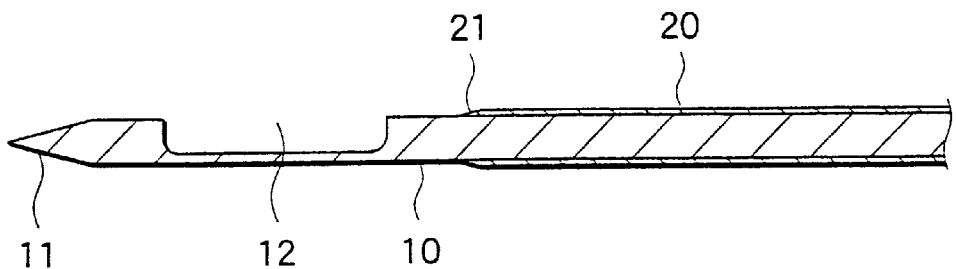
FIG. 31 is a longitudinal section showing the distal end portion of a related endoscopic tissue collecting instrument.
Figure 32:
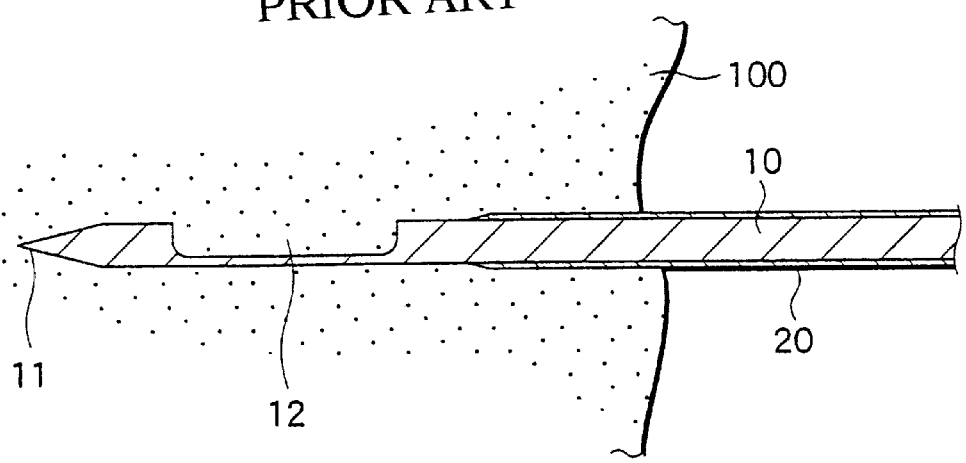
FIG. 32 is a longitudinal section showing the distal end portion of the related endoscopic tissue collecting instrument as it is in the first phase of use.
Figure 33:
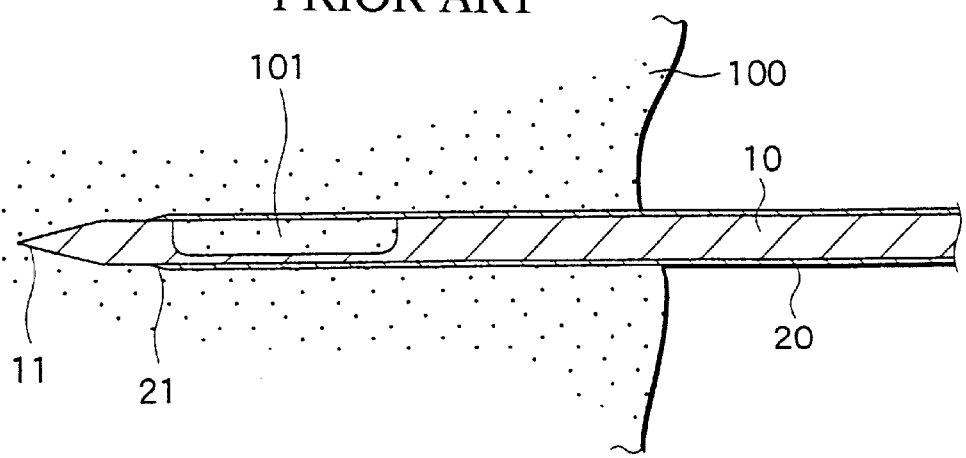
FIG. 33 is a longitudinal section showing the distal end portion of the related endoscopic tissue collecting instrument as it is in the second phase of use.
Figure 34:
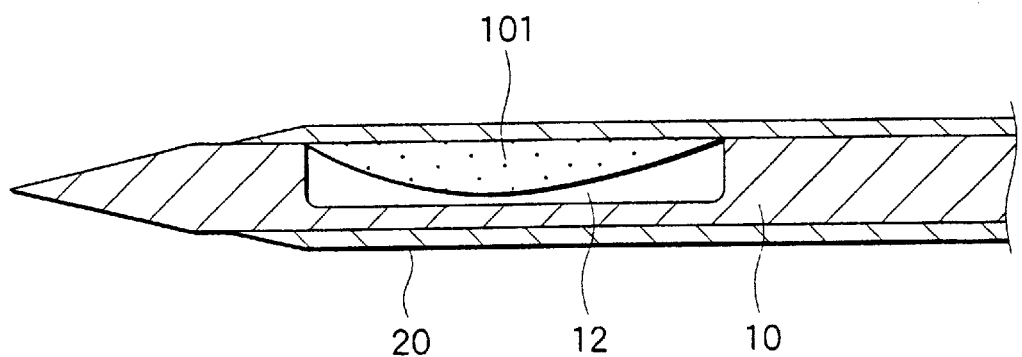
FIG. 34 is a longitudinal section showing enlarged a problem which occurs when a tissue specimen is collected with the related instrument.
Figure 35:
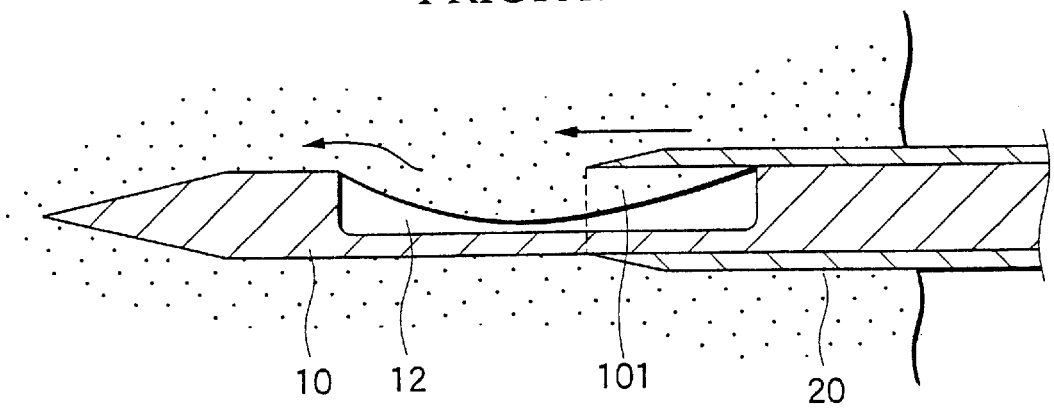
FIG. 35 is a longitudinal section showing enlarged another problem which occurs when a tissue specimen is collected with the related instrument.

FIG. 29 shows another modification in which the needle shaft 310 is made of a piping which is fitted with another part that serves as the needle tip 311. Alternatively, the distal end of the piping may be cut at an angle to form the needle tip 311 as shown in FIG. 30.

What is claimed is:

1. An endoscopic tissue collecting instrument comprising:
a needle shaft with a tip pointed forward, that has a tissue retaining recess formed in a lateral side of an area close to the tip;
an outer sheath that is fitted over the needle shaft to be capable of moving back and forth and which has a blade formed at a distal end to cut off a tissue retained in the recess; and
a fixing member that is engageable with basal end portions of the needle shaft and the outer sheath and which can be securely connected to or disconnected from an entrance of a treatment instrument insertion channel in an endoscope.

2. The instrument according to claim 1, wherein each of the needle shaft and the outer sheath has flexibility.

3. The instrument according to claim 1, wherein the tip of the needle shaft projects by a predetermined length from an exit of the treatment instrument insertion channel when the basal end portion of the needle shaft is brought into engagement with the fixing member and the fixing member is securely connected to the entrance of the treatment instrument insertion channel.

4. The instrument according to claim 2, wherein the basal end portion of the outer sheath is capable of coming into or out of engagement with the fixing member independently of the needle shaft.

5. The instrument according to claim 4, wherein the fixing member is provided with an urging member, and the outer sheath is pushed and moved along a longitudinal axis by the urging member if the outer sheath is brought out of engagement with the fixing member.

6. The instrument according to claim 1, wherein the fixing member has first part which is to be securely connected to the entrance of the treatment instrument insertion channel, and second part which is to be engaged with the needle shaft and the outer sheath, the first part can be securely connected to or disconnected from the second part, and when the first part is disconnected from the second part, the needle shaft and the outer sheath can be moved back and forth as an integral unit along the longitudinal axis.

7. The instrument according to claim 1, further comprising:
an aspiration channel that communicates with the tissue retaining recess in a distal end portion and which extends to the basal end portion of the needle shaft.

* * * * *